United States Patent [19]

Jiang

[11] Patent Number: 5,202,482
[45] Date of Patent: Apr. 13, 1993

[54] MALIGNANCY-ASSOCIATED CATABOLITE

[75] Inventor: Bing D. Jiang, Indianapolis, Ind.

[73] Assignee: Oncologic Labs, Inc., Tenafly, N.J.

[21] Appl. No.: 420,931

[22] Filed: Oct. 13, 1989

[51] Int. Cl.⁵ ............................................ C07C 211/00
[52] U.S. Cl. ...................................... 564/1; 564/463;
514/579; 514/663; 514/762
[58] Field of Search .................... 436/64, 86, 89, 813;
435/12; 564/1, 463; 514/579, 663, 763

[56] References Cited

PUBLICATIONS

Halpern et al., Proceeding of the National Academy of Science, vol. 74, pp. 587–591, 1977.
D. Handt et al., European Journal of Biochemistry, vol. 200, pp. 237–244, 1991.
Lehninger, Biochemistry (2nd Ed.), Worth Publishers, Inc., New York, N.Y. (1975), at p. 311.
The Merck Index (11th Ed.), The Merck Co., Rahway, N.J. (1989), at p. 24.

*Primary Examiner*—Jose G. Dees
*Assistant Examiner*—D. D. Carr
*Attorney, Agent, or Firm*—Charles J. Herron

[57] ABSTRACT

The present invention arises from the discovery of an endogenous malignancy-associated catabolite characterized by (i) a molecular weight of about 135 daltons as determined by mass spectrum analysis; (ii) a UV absorption maximum at 237 nm; (iii) a 15 centimeter C18 HPLC column retention time of from about 1.00 to about 2.00 minutes as compared to a retention time at a 1 ml/minute flow rate of about 2.5 to about 3.0 minutes for an internal standard marker; (iv) containing no aromatic ring structures, containing one methyl group at the 1-position and one methyl group at the 6-position of an alpha carbon chain, and containing at least one nitrogen moiety as determined by nuclear magnetic resonance; and (v) being present in elevated amounts in the urine substantially exclusively of individuals suffering from malignant conditions. Further, the invention provides a method of monitoring the effectiveness of treatment of an individual treated for a malignant condition and a method for determining the presence or absence of a malignant condition in an individual, which methods comprise analyzing a urine sample of the individual for the concentration of malignancy-associated catabolite therein.

1 Claim, 1 Drawing Sheet

MALIGNANCY-ASSOCIATED CATABOLITE

BACKGROUND OF THE INVENTION

1. Field of the Invention

The present invention relates to a newly observed catabolite in a body fluid, particularly urine, its association with malignant conditions in those individuals in which it is present in elevated amounts and methods and materials for its detection.

2. Brief Description of the Prior Art

Numerous methods and markers to determine the presence of cancer cells in mammals, including humans, and to monitor the progress of its treatment have been proposed. Senger, et al, U.S. Pat. No. 4,725,538 discloses observation of a 70,000–74,000 molecular weight protein marker. Burzynski, U.S. Pat. No. 4,444,890 discloses a method for the determination in physiological tissues or fluids of antineoplastons, a group of peptides and amino acid derivatives said to be capable of modulating neoplastic disease. DeFazio et al, U.S. Pat. No. 4,447,545 discloses a method of screening for bladder cancer based on a correlation between the respective ratios of C-reactive protein to total protein in urine and serum and the incidence of bladder cancer. Matsumoto et al., U.S. Pat. No. 4,757,003 discloses a method of cancer detection by immunoassay for certain identified glycolipids which have been found to increase in body fluids with a proliferation of cancer cells. Vold, U.S. Pat. No. 4,665,018 discloses that human cancer can be diagnosed/monitored by measuring the levels of certain modified nucleosides, such as N-[(beta-D-ribofuranosyl)purin-6-ylcarbamoyl]-L-threonine, in urine by a quantitative immunoassay that preferably employs a monoclonal anti-modified nucleoside antibody.

In addition to the above patents, many publications have reported that individuals having diagnosed malignancies are known to excrete high concentrations of certain catabolites, such as p-acetamidobenzoate and pterine derivatives, in their urine. For example, Halpern et al., *Pterin-6-aldehyde, a Cancer Cell Catabolite: Identification and Application in Diagnosis and Treatment of Human Cancer*, Proc. Nat. Acad. Sci. USA, 74:587–591(1977) report the excretion and identification of pterin-6-aldehyde in the culture media of malignant cells, but not in the media of adult normal cells, embryonic cells and amniotic cells. It was also shown by thin-layer chromatography to be present in the urine of cancer patients (concentrations greater than 300 nmol/ml) but not in normals. Pterin-6-carboxylate and pterin but not pterin-6-aldehyde have previously been found in human urine. Rokos et al., *Altered Urinary Excretion of Pteridine in Neoplastic Disease*, Clin. Chim. Acta., 105:275–286(1980) reports finding elevated levels of neopterin in 70% of cancer patients studied. Biopterin was less frequently increased and xanthopterin was generally raised when neopterin and/or biopterin excretion was high. They concluded that the pathogenic, diagnostic and therapeutic significance of these changes remains to be established.

Stea et al., *Urinary Excretion Levels of Unconjugated Pterins in Cancer Patients and Normal Individuals*, Clin. Chim. Acta., 113:231–242(1981) report observing a significant increase in the excretion of xanthopterin, neopterin and pterin and a significant decrease in isoxanthopterin. They also report that biopterin levels were only slightly increased and excretion levels of pterin-6-carboxylic acid and 6-hydroxymethylpterin were about equal in cancer patients and normals. They conclude that excretion patterns of pterins appear to correlate with clinical status and that a definite imbalance in pterin, and possibly folate metabolism, is associated with the presence of malignant diseases.

Rao et al., *Elevated Urinary Levels of 6-hydroxymethylpterin during malignancy and liver regeneration: a Simple, Non-invasive test for Cancer Detection*, Cancer, 48:1656–1663(1981) report a method for determining urinary 6-hydroxymethylpterin levels. Using this method, healthy human subjects were found to excrete this compound at a mean level of 0.121 ug/ml of urine, while patients with various types of cancer excreted levels ranging from 0.3 to 2.0 ug/ml. The mean excretion level for patients with nonmalignant diseases was 0.134 ug/ml. Trehan et al., *Urinary 6-Hydroxymethylpterin Levels Accurately Monitor Response to Chemotherapy in Acute Myeloblastic Leukemia*, Cancer, 50:114–117(1982) report measuring urinary 6-hydroxymethylpterin levels as an index of disease status in acute myeloblastic leukemia patients on antileukemic drugs.

In contrast, Hausen et al., *Urinary pteridines in Patients Suffering from Cancer*, Cancer, 53:1634–1636(1984) reports that the levels determined by Rao et al and Trehan et al were of various pteridines and not exclusively 6-hydroxymethylpterin as reported. Hausen et al also take the position that the urinary component which correlates to the status of malignant disease is neopterin.

Jiang et al., *Analysis of Urinary Fluorescent Compounds for Cancer Detection*, Chin. Med. J., 98:495–496(1985) report a favorable evaluation of the fluorescence detection method described by Rao et al and Trehan et al which they used with minor modifications.

Tamura et al., *Urinary Excretion of Pseudouridine in Patients with Hepatocellular Carcinoma*, Cancer, 57:1571–1575 (1986) reports the urinary concentration of pseudouridine in 16 of 23 patients with hepatocellular carcinoma was significantly higher than in patients with cirrhosis of the liver or healthy controls.

Borek, E., *Toward a universal tumour marker*, Tumour Biol., 5(1):1–14 (1984) and Borek etal., Recent Results in Cancer Research, 84:301–316 (19 ) review work in examining nucleosides as tumor markers. These markers are derivatives of abnormal transfer RNA derivatives and include methylated purine, methylated pyrimidine, pseudouridine, 2-pyridone-5-carboxamide-N'-ribofuranoside and Beta-aminoisobutyric acid. This approach, as well as the others described, requires extensive purification of the sample prior to analysis by HPLC. For other articles regarding nucleosides as tumor markers, see Fischbein, et al., Cancer Detect Prev., 7(4):247–252 (1984); Kaneko, et al., Biochem Biophys Acta, 802(2):169–174 (1984); Sharma, et al., Cancer Detect Prev., 6(1-2):77–85 (1985); Borek, et al., Cancer Detect Prev., 6(1-2):67–71 (1983); Borek, et al. Am. J. Obstet Gynecol., 146(8):906–910 (1983) and other earlier publications by these workers.

Notwithstanding the efforts reported above, such methods as are available are not suitable for routine clinical testing, such as in screening programs. Recent approaches to isolating and identifying tumor markers have required extensive procedures as described above. Also, while some of the methods require complicated specimen processing, others either lack sufficient sensitivity or have a high rate of false positive results reported.

SUMMARY OF THE INVENTION

The present invention arises from the discovery of an endogenous malignancy-associated catabolite (MAC) characterized by (i) a molecular weight of about 135 daltons as determined by mass spectrum analysis; (ii) a UV absorption maximum at 237 nm; (iii) using a 15 centimeter C18 type HPLC column at 1 ml/minute flow rate has a retention time of from about 1.00 to about 2.00 minutes as compared to a retention time of about 2.5 to about 3.0 minutes for an internal standard marker; (iv) containing no aromatic ring structures, containing one methyl group at the 1-position and one methyl group at the 6-position of an alpha carbon chain, and containing at least one nitrogen moiety as determined by nuclear magnetic resonance; and (v) being present in elevated amounts in the urine substantially exclusively of individuals suffering from malignant conditions.

Further, the invention provides a method of monitoring the effectiveness of treatment of an individual treated for a malignant condition and a method for determining the presence or absence of a malignant condition in an individual, which methods comprise analyzing a urine sample of the individual for the concentration of malignancy-associated catabolite therein.

Malignancy-associated catabolite is considered as a positive test result indicative of malignant conditions when a predetermined amount of patient urine when analyzed by HPLC gives a peak height (concentration) of MAC which is at least about 2.5 times greater than the peak height (concentration) of a predetermined amount of, an internal standard compound, such as 5-fluorouracil when used as a reference standard analyzed in the same manner. For example, a 0.2 ul urine sample when analyzed by HPLC with the conditions described below gives a peak height (concentration) of MAC which is at least 2.5 times greater than the peak height (concentration) of 1 ug of 5-fluorouracil when used as a reference standard analyzed in the same manner.

DETAILED DESCRIPTION OF THE INVENTION

Figure 1A:
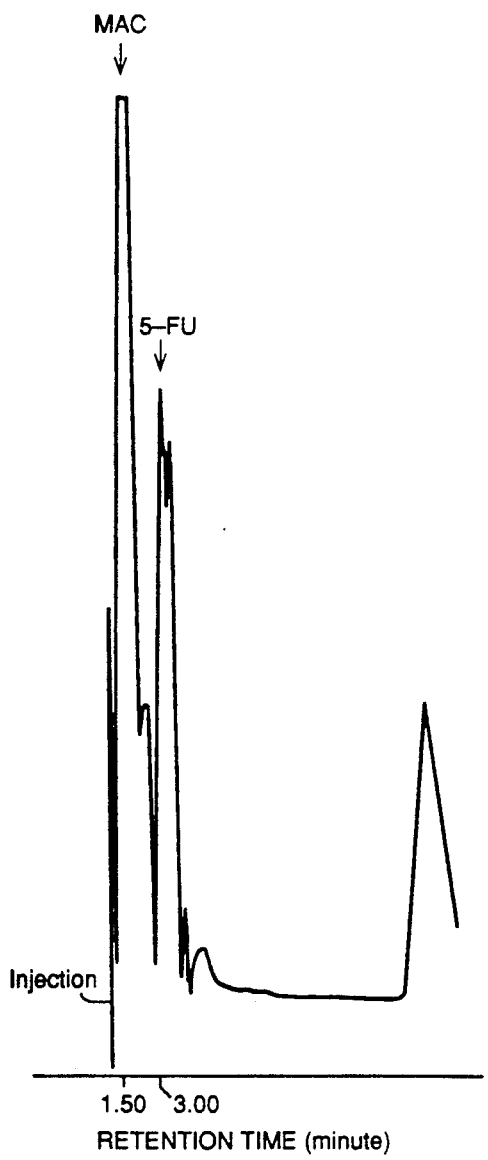
FIG. 1A is a graphical illustration of the relative amounts and retention times of MAC and the 5-fluorouracil in a positive test result included in the clinical study reported in Example 3.

In the development of this invention, urine specimens were obtained from hundreds of human patients to be assayed for the presence of malignant conditions or cancer patients already undergoing treatment (surgery, chemotherapy or radiotherapy) and were assayed by the disclosed methods applicable to diagnosis of malignant conditions or for monitoring the effectiveness of a regimen of therapy in a cancer patient.

The assay procedures in accordance with the invention offer several advantages over other tumor marker determinations previously reported or available, including the following particularly significant advantages.

1. No pretreatment or special processing of the urine samples is necessary. Most, if not all, of the other methods required complicated specimen preparation before the assay could be performed.

2. Less than about 10 microliters (ul) or less of urine specimen is required. The MAC substance is present in such elevated amounts in cancer patients that, in fact, the urine samples can be diluted 50-fold in water for use in the HPLC assay, effectively making the amount of urine per sample only 0.2 ul of urine.

3. No complicated buffer is needed for the HPLC assay. Water is a perfectly acceptable medium for the mobile phase of the HPLC assay, although conventional buffers can also be used. No other reported or available test uses water as the mobile phase for HPLC.

4. In general, the HPLC column can be reused repeatedly for about 500 runs without washing and regeneration between samples. However, a wash after a positive sample is needed.

5. Each test takes only about five (5) minutes, much more rapid than any other cancer detection test reported or available.

6. Many peaks can appear in an HPLC analysis. Only the single peak appearing at 1.00-2.00 minutes has diagnostic value in accordance with the method described herein.

7. Approximately 80% of all cancers can be detected by the simple screening method disclosed.

Analysis of the MAC compound by nuclear magnetic resonance (NMR) has provided observations that it contains no aromatic ring structures, that it contains one methyl group at the 1-position and one methyl group at the 6-position of an alpha carbon chain, and that it contains at least one nitrogen moiety. Thus, this clearly demonstrates that the MAC substance is not a nucleoside or nucleotide such as the potential tumor markers examined by Borek etal. and Tamura et al. Since the maximal absorbance of this compound is at 237 nm, it cannot be a pterin or other fluorescent compound, such as those reported by Stea or Halpern et al.

In a preferred embodiment, the method for determining the presence or absence of a malignant condition in an individual which comprises observing the presence of a malignancy-associated catabolite for which the ratio of the amount thereof as compared to the amount of a marker, such as 5-fluorouracil, pseudouridine, adenosine triphosphate, adenosine or isoleucine, in a urine sample therewith is present in a ratio of at least about 2.5:1 in individuals having malignant or premalignant conditions, which method comprises the following steps:

a. preparing an aqueous solution containing a predetermined number of microliters of said urine and a predetermined amount of the marker as reference standard;

b. passing the aqueous solution so-prepared through a C18-type HPLC column;

c. observing the relative amounts of the malignancy-associated catabolite and the marker which are eluted from the HPLC column; and d. determining the ratio of concentrations of the malignancy-associated catabolite and the marker.

Also in a preferred embodiment, the method for monitoring the effectiveness of treatment of an individual treated for a malignant condition which comprises observing the concentration before and after said treatment of a malignancy-associated catabolite for which the ratio of the amount thereof as compared to the amount of marker in a urine sample therewith prior to said treatment is present in a ratio of at least about 2.5:1 in individuals having a malignant condition, which method comprises the following steps:

a. preparing an aqueous solution containing a predetermined number of microliters of said urine and a predetermined amount of marker as a reference standard;

b. passing the aqueous solution so-prepared through a C18-type HPLC column;

c. observing the relative amounts of the malignancy-associated catabolite and the marker which are eluted from the HPLC column; and d. determining the ratio of concentrations of the malignancy-associated catabolite and the marker.

Preferably, preparing the aqueous solution comprises diluting a urine sample 50-fold with water; adding 1 microgram of marker to 10 ul of the diluted sample to provide a test preparation; passing the 10 ul test preparation so-prepared through a 15 centimeter HPLC C-18 type column at a flow rate of about 1.0 milliliters/minute.

Also preferably, observing the relative amounts of the malignancy-associated catabolite and the marker which are eluted from the HPLC column comprises so-observing by ultraviolet detection at 240 nanometers wavelength; observing the relative amounts of the malignancy-associated catabolite and the marker which are eluted from the HPLC column comprises so-observing the elution, from a 15 centimeter HPLC column through which the liquid phase is passing at a flow rate of about 1.0 milliliters/minute, of malignancy-associated catabolite at an elution running time of about 1.0 to 2.0 minutes and of marker at an elution running time of about 2.5 to 3.0 minutes. Preferably, determining the ratio of the malignancy-associated catabolite and the marker comprises determining the relative concentrations thereof by dividing the observed peak height value of the malignancy-associated catabolite by that of the marker.

Certain conditions are especially preferred relating to the testing procedure. They include preferential use of first morning urine specimens and storage of specimens under refrigeration conditions (e.g., −20° C. or colder) if they are not to be assayed immediately.

Three types of individuals are not suitable for testing using the disclosed MAC substance and methods, because of an observed risk of false positive results. They are patients younger than about 12 years of age, patients with nephritis or rheumatoid arthritis or patients taking certain Chinese herbal medicines, especially ginsen.

In addition to the HPLC assay described and exemplified herein, it is well within the skill of those in the field of immunology, once provided with an awareness of the existence and identifying characteristics of the MAC to prepare a polyclonal or monoclonal antibody thereto and, with that antibody, prepare an immunoassay composition and perform the immunoassay in any of the many known immunoassay methodologies, including competitive and noncompetitive, radioisotopic and nonradioisotopic, soluble and insoluble, and particularly preferably homogeneous immunoassays using any of the foregoing which is known to be appplicable.

It is also within the skill of those knowledgeable in the field of clinical chemistry, once provided with an awareness of the existence and identifying characteristics of the MAC to develop a chemical method for quantitative determination of the MAC. These can be methods suitable for hospital, doctor's office or home use and can be in liquid format or in the form of test strips or analytical elements.

EXAMPLE 1

Characterization of the Malignancy-Associated Catabolite

The experiments reported by this example illustrate the method by which MAC was identified and initially characterized and provides a method of distinguishing MAC from other compounds.

Analytical Procedure

High pressure liquid chromatography (HPLC) analyses of urine samples were carried out using a Varian 5060 high pressure liquid chromatography system (Varian Assoc., Palo Alto, Calif.), using a ready-to-use reverse phase C-18 type column packed with a molecular sieving compound. Here, a 15 cm MCH-5 column (Varian Associates) was employed at 30° C. The internal control compound was 5-fluorouracil (molecular weight of 133).

Urine samples were collected from human volunteers at random times, however a first morning urine is preferred, and were used in this procedure without pretreatment. To begin the procedure, urine (10 ul) was injected into the top of the column. The column was then eluted with degassed distilled water at a flow rate of 1.0 ml/min. This purification was repeated several times until milligram quantities of MAC were obtained.

Results

Figure 1B:
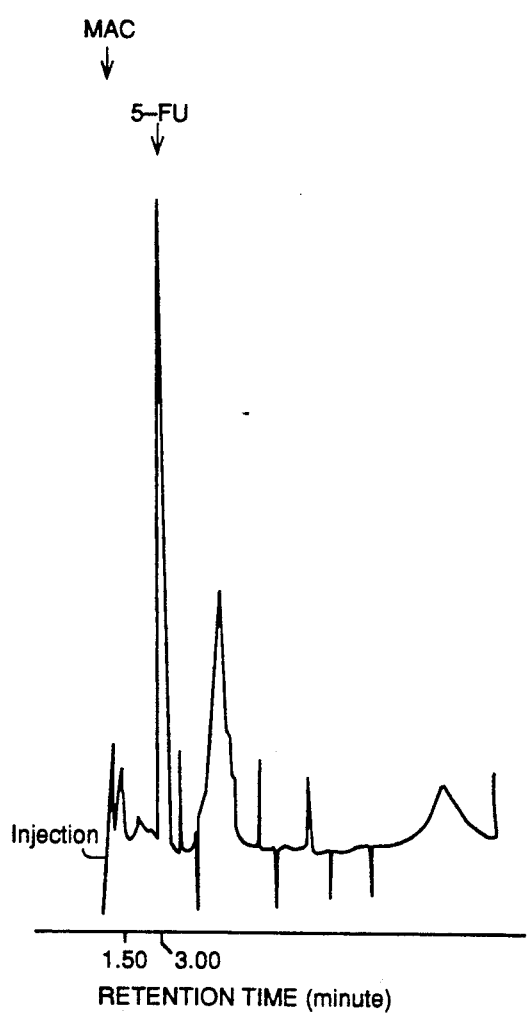
FIG. 1B is a graphical illustration of the relative amounts and retention times of MAC and the 5-fluorouracil in a negative test result included in the clinical study reported in Example 3.

The internal control compound (1 ug of 5-fluorouracil in 10 ul of the diluted sample) produced a peak of 15,000 units in height with a retention time of 3.00 minutes, as shown in FIGS. 1A and 1B. The compound of the present invention was eluted at 1.50 minutes under the same conditions, as shown in FIG. 1A. The relative concentration of the compound of the invention in the urine was determined by dividing the value of the peak height of the MAC compound by the peak height of the reference compound. The numerical values of the peak heights are arbitrary units which will depend on the particular instrument use for the assay.

Mass-Spectrometric Analysis

The compound of the present invention, purified from urine samples of cancer patients by HPLC as described above, was then subjected to mass-spectrometric analysis. The results revealed a molecular weight of 135 daltons.

Spectrophotometric studies were performed on the compound observed in accordance with the invention as well as on numerous other organic compounds, including xanthopterine, creatinine, uracil, riboflavin, aminopterine, neopterine, 6-hydroxymethylpterine, vitamins $K_1$ and C, uric acid and adenine.

These studies revealed a maximal ultraviolet absorbance by the MAC substance at a wavelength of 237 nanometers. Adenine was the only compound found to have a similar retention time on HPLC and is known to have a molecular weight of 135 daltons. However, because its maximal UV absorbance is at 260 nm, rather than at 240 like the compound observed in accordance with the invention, the compound associated with malignancy by the present invention is not adenine.

EXAMPLE 2

Detection of Malignancy-Associated Catabolite

Analytical Procedure

First morning urine specimens were collected, placed on ice, and subjected to high pressure liquid chromatography (HPLC) analysis as follows. The urine was diluted fifty (50) times with water, and 5-fluoro-uracil (5-FU) was added to a final concentration of 1 ug/10 ul. Then, 10 ul of the diluted specimen containing 1 ug 5-FU was injected into a 15 cm long C-18 type HPLC column. A Varian HPLC machine (Model 5060) with a recorder (Spectra Physics, Inc.) was used. HPLC was run at 30° with a flow rate of 1.0 ml/minute using degassed, distilled water as the mobile phase. The eluate was passed through an ultraviolet (UV) detector set to a wavelength of 240 nm. Each HPLC was run for 5 minutes. Usually, no washing and regeneration of the column is needed between samples. However, it is necessary to wash the column for 10 minutes with water after a positive sample. A column can be reused for about 500 runs.

The amount of 5-FU (1 ug) injected into the column usually gives a peak at about 2.5–3.0 minutes with a peak height of 10,000 to 20,000 units depending on the machine used. The malignancy-associated catabolite (MAC) usually gives a peak at about 1.0–2.0 minutes. The relative concentration of MAC present in the urine samples was determined by dividing the value of peak height of the MAC by that of 5-FU.

Results

The urine sample of a patient with a malignant brain tumor (FIG. 1A) gave the following results. The 5-FU peak appeared at 3.00 minutes with a peak height of about 15,000. The MAC peak appeared at 1.50 minutes with a peak height of about 68,885.

The urine sample of a patient with alcoholic liver cirrhosis (FIG. 1B) gave the following results. The 5-FU peak appeared at 3.00 minutes with a peak height of about 15,000. No MAC peak was detected.

Conclusion

Urine specimens from cancer patients have a unique peak appearing at about 1.0–2.0 minutes in the above HPLC assay. This peak is not usually found in the urines of normal individuals or non-cancer patients, or is the MAC is present in relatively small amounts. The peak height of MAC in a non-cancer patient is less than about 2.5 times that of the peak height of 1 ug of 5-FU assayed as described above.

EXAMPLE 3

Clinical Correlation of the Malignancy-Associated Catabolite

Human Subjects

Healthy individuals were volunteers who had no complaints of illness and no clinical signs upon physical examination. Neoplastic disorders were diagnosed by various methods including laboratory tests, gross examination of biopsies and resected tissue, and electron microscopic examination of tissue sections. Non-cancer disorders were diagnosed by routine laboratory tests and physical examination. HPLC analysis was performed as described in the preceding example.

Results

Five hundred (500) urine specimens from healthy individuals and from patients with various diseases were examined for the presence of MAC by the above HPLC procedure. Among 143 cancer cases included in the sample population, 122 cases (85.3%) gave positive results upon analysis for MAC, as shown in Table 1.

TABLE 1

| MAC Analysis in Healthy, Cancer and Non-Cancer Individuals | | | |
|---|---|---|---|
| Groups | Total | MAC/5-FU = < 2.5 | MAC/5-FU > 2.5 |
| Cancer | 143 | 21(14.7%) | 122(85.3%) |
| Non-cancer | 209 | 208(99.5%) | 1(0.5%) |
| Healthy | 119 | 119 | 0 |
| Treated Cancer | 29 | 29 | 0 | p < 0.001 (t-test, cancer group vs non-cancer group + healthy)

The positive results were particularly high in patients with carcinomas of the liver, stomach and nasopharynx, as shown in Table 3.

TABLE 2

| MAC Analysis on Patients with Neoplasms | | |
|---|---|---|
| Cancer Site | Total | MAC > 0.558 ug/10 ul |
| liver | 23 | 22 (95.6%) |
| stomach | 28 | 27 (96.4%) |
| nasopharynx | 3 | 3 (100%) |
| lung | 44 | 34 (77.2%) |
| esophagus | 6 | 5 (83.3%) |
| cervix | 4 | 3 (75%) |
| breast | 5 | 5 (100%) |
| lymphoma | 6 | 5 (83.3%) |
| leukemia | 6 | 5 (83.3%) |
| colon | 3 | 3 (100%) |
| others | 15 | 10 (66.6%) |
| Total | 143 | 122 (85.3%) |

Urine specimens from 208/209 (99.5%) non-cancer patients were negative for MAC assay. The one urine sample which gave a false positive reaction was from a patient with acute nephritis. Patents in the non-cancer group included those with pulmonary tuberculosis, pneumonia, hepatitis, cirrhosis, gastritis, various non-malignant tumors and other diseases. No difference in response is observed based on the sex of the individual.

Conclusion

Approximately 85% of the urine specimens from patients with neoplasms contained high concentrations of MAC which can be detected as a unique peak using HPLC.

EXAMPLE 4

Monitoring of Treatment Response

In order to determine whether MAC concentration decreased after treatment, urine samples from 30 cancer patients who had recovered after treatment were assayed for MAC. The treatments included surgery, chemotherapy and radiation. Surgically treated cancers included 6 breast, 9 stomach, 3 thyroid gland, 3 colon, 2 bladder, 1 liver and 1 skin cancers. Two patients with malignant lymphoma received chemotherapy. One seminola, 1 nasopharynx and 1 esophageal cancer patients were treated by radiation. The urines from these 30 patients were all negative for MAC.

By way of example, one of the patients in the extensive clinical study reported as an example herein, rather than having been first reported to the clinical community in the literature, is one having a hepatoma of the liver treated by liver transplant. The MAC peak in the patient's urine after treatment had decreased to a level considered within the range of normal (negatives).

What is claimed is:

1. An endogenous malignancy-associated catabolite characterized by:
   (i) a molecular weight of about 135 daltons as determined by mass spectrum analysis;
   (ii) a UV absorption maximum at 237 nm;
   (iii) a 15 centimeter C18-type HPLC column retention time at a 1 ml/minute flow rate of from about 1.00 to about 2.00 minutes as compared to a retention time of about 2.5 to about 3.0 minutes for an internal standard marker;
   (iv) containing no aromatic ring structures, containing one methyl group at the 1-position and one methyl group at the 6-position of an alpha carbon chain, and containing at least one nitrogen moiety as determined by nuclear magnetic resonance; and
   (v) being present in elevated amounts in the urine substantially exclusively of individuals suffering from malignant or premalignant conditions, other than those younger than about 12 years of age, having nephritis or rheumatoid arthritis or who are taking Chinese herbal medicines.

* * * * *